United States Patent [19]

Hymes et al.

[11] 4,307,717

[45] Dec. 29, 1981

[54] STERILE IMPROVED BANDAGE CONTAINING A MEDICAMENT

[75] Inventors: Alan C. Hymes, Hopkins; Lincoln T. Ong, Minnetonka; Garry R. Persons, Edina, all of Minn.

[73] Assignee: LecTec Corporation, Eden Prairie, Minn.

[21] Appl. No.: 173,001

[22] Filed: Jul. 28, 1980

Related U.S. Application Data

[63] Continuation-in-part of Ser. No. 58,684, Jul. 18, 1979, which is a continuation-in-part of Ser. No. 950,625, Oct. 12, 1978, which is a continuation-in-part of Ser. No. 849,405, Nov. 7, 1977, Pat. No. 4,125,110.

[51] Int. Cl.³ ............................................. A61L 15/00
[52] U.S. Cl. ..................................... 128/156; 424/26; 106/124; 260/29.1 R; 428/343
[58] Field of Search ................................ 128/155–156, 128/283, 640–641; 424/28, 26, 31; 106/124, 205, 210, 129, 227; 260/29.1 R; 428/261, 343

[56] References Cited

U.S. PATENT DOCUMENTS

| | | | |
|---|---|---|---|
| 3,249,109 | 5/1966 | Maeth et al. | 128/156 |
| 3,475,363 | 10/1969 | Gander | 428/343 |
| 3,612,053 | 10/1971 | Pratt | 128/283 |
| 3,640,741 | 2/1972 | Etes | 128/283 |
| 3,946,730 | 3/1976 | Monter | 128/641 |
| 3,972,995 | 8/1976 | Tsuk et al. | 128/156 |
| 4,253,460 | 3/1981 | Chen et al. | 128/156 |

FOREIGN PATENT DOCUMENTS

| | | | |
|---|---|---|---|
| 495110 | 8/1977 | Australia | 128/156 |
| 2919923 | 11/1979 | Fed. Rep. of Germany | 128/156 |

*Primary Examiner*—C. Fred Rosenbaum
*Attorney, Agent, or Firm*—Williamson, Bains, Moore & Hansen

[57] ABSTRACT

A flexible, liquid absorbent, adhesive bandage includes a backing element and a substrate attached to the backing element. The substrate comprises a homogeneous, hydrophilic, stable matrix including a solid phase formed of a synthetic polymer, a long chain polysaccharide, or a combination thereof. The liquid phase of the matrix consists of a hydric alcohol, carbohydrates and/or proteins in an aqueous solution, and/or water or a combination thereof. The matrix contains a medicament therein for release to the affected areas.

13 Claims, 4 Drawing Figures

STERILE IMPROVED BANDAGE CONTAINING A MEDICAMENT

BACKGROUND OF THE INVENTION

The present application is a continuation-in-part of U.S. application Ser. No. 58,684, filed July 18, 1979, entitled, "AN IMPROVED MONITORING STIMULATION ELECTRODE". U.S. patent application Ser. No. 58,684, is a continuation-in-part of U.S. patent application Ser. No. 950,625 filed Oct. 12, 1978, which in turn, is a continuation-in-part of U.S. patent application Ser. No. 849,405, filed Nov. 7, 1977, now U.S. Pat. No. 4,125,110 issued Nov. 14, 1978, and entitled, "MONITORING AND STIMULATION ELECTRODE".

Attempts have been made to develop bandages which are self-adhesive, absorbent and sterile. For example, U.S. Pat. No. 3,339,546, discloses a self-adhesive bandage which is adapted to adhere to a moist surface such as the moist mucosa of the oral cavity. However, one of the essential materials of this self-adhesive bandage is an adhesive gum, preferably polyisobutylene, which is hydrophobic. Similarly, U.S. Pat. Nos. 3,598,122, 3,598,123 disclose bandages which contain drugs that are continually released from an adhesive layer. These bandages are formed of layered materials which have encapsulated in the adhesive layer. Even though the bandage disclosed in these prior art patents are said to be self-adhesive and are satisfactory vehicles for drugs, it is not believed that these bandages can be effectively sterilized. In this regard, it is pointed out that these bandages should not only be capable of protecting and releasing the medicaments to the affected area, but in most applications it is an essential requirement that the bandage be sterile. The only practical sterilization technique is by irradiation and it is not believed that the prior art bandages can be irradiated without affecting the adhesive characteristics and dimensional stability thereof.

SUMMARY OF THE INVENTION

Therefore, it is a general object of this invention to provide a sterile, self-adhesive, novel bandage in which medicament is molecularly dispensed for release to the affected area. The bandage is comprised of a flexible backing element and a self-adhesive substrate which becomes increasingly tacky in the presence of moisture and which absorbs liquid and releases the medicament to the affected area while remaining dimensionally stable during such absorption. Sterilization may be accomplished by irradiation with only a minimal effect on the dimensional stability of the substrate.

These and other objects and advantages of this invention will more fully appear from the following description made in connection with the accompanying drawings, wherein like reference characters refer to the same or similar parts throughout the several views.

FIGURES OF THE DRAWINGS

DESCRIPTION OF THE PREFERRED EMBODIMENT OF THE INVENTION

The bandage of the present invention has adhesive properties for maintaining contact with the skin, as well as, possessing a certain amount of elasticity for movement with the skin. The bandage is intended to be easily handled and in all respects is non-irritating to the patient.

Figure 1:
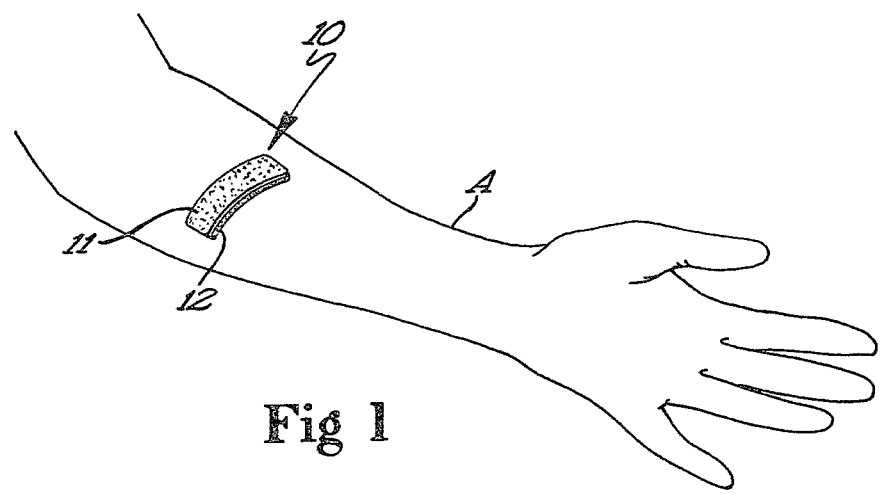
FIG. 1 is a perspective view illustrating the novel bandage applied to the arm of a patient.
Figure 2:
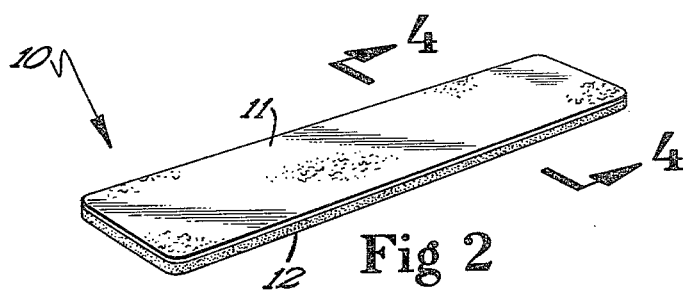
FIG. 2 is a perspective view of a bandage illustrated in FIG. 1.
Figure 3:
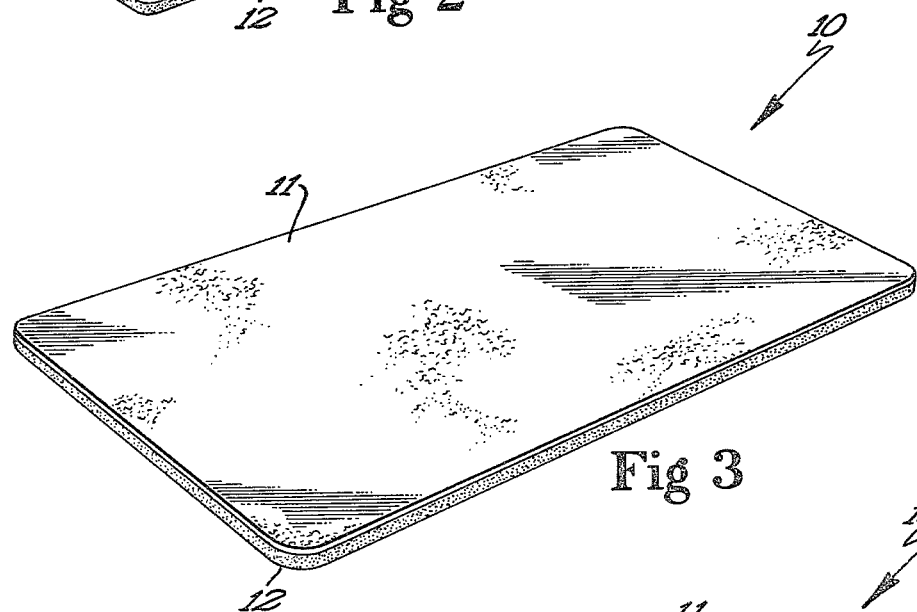
FIG. 3 is a perspective view of the bandage used as a surgical dressing.
Figure 4:
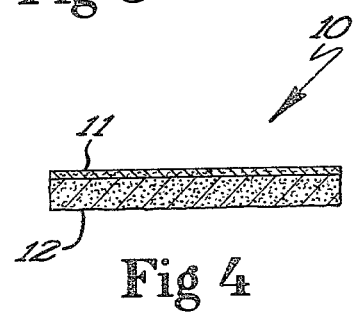
FIG. 4 is a cross-sectional view taken approximately along line 4—4 of FIG. 2 and looking in the direction of the arrows.

Referring now to the drawings, it will be seen that the bandage of the present invention is thereshown. The bandage, designated generally by the reference numeral 10 includes a backing member 11 and a self-adhesive substrate 12 which is secured to one surface of the backing. The backing element 11 and the substrate 12 are both illustrated as rectangular sheets of material of uniform thickness. It is pointed out that the bandage 10 is intended to be of uniform thickness but may have any other configuration although the rectangular shape is preferred. In use, the bandage is applied with the substrate 12 in direct contact with the skin to cover a non-surgical wound, a surgical wound, or burned tissue. In FIG. 3, the embodiment illustrated therein is a surgical dressing and will be applied to the patient to cover a surgical wound.

Primary to the unique structure of the bandage is the hydrophilic adhesive properties of the substrate which enhance the adhesion thereof to the skin. The substrate not only absorbs moisture making it ideal for use as a surgical dressing, but the substrate becomes tackier as it absorbs moisture.

The substrate 12 may be formed from naturally occurring materials such as karaya powder, guar gum, gum acacia, carboxypropylcellulose, locust bean gum, and other polysaccharides. The substrate may also be formed from synthetic polymers such as poly-acrylic acid, poly-acrylamide and their cogeners, poly-acrylic acid molecular weights 250,000, 450,000, 1,000,000 and 4,000,000, and poly-acrylamide sold under such trademarks as Reten by the Hercules Co. When monomers such as acrylic acid or acrylamide are polymerized, it is necessary to use activators. Activators, which are used during polymerization, may include ferrous sulfate, sodium metabisulfite, potassium persulfate, and N'N'methylene bis-acrylamide as set forth in my copending application, Ser. No. 58,684. The disclosure of my copending application Ser. No. 58,684 is incorporated by reference herein.

The synthetic and/or natural gums constitute the solid phase of the matrix. The liquid phase of the matrix preferably consists of hydric alcohols such as glycerol or propylene glycol. Solutions or emulsions of saccharides and/or poly-saccharides and/or proteins may be used in forming the matrix. Alternatively, a combination of a solution or emulsion of polysaccharides, saccharides or proteins may be used in the liquid phase of the matrix.

The substrate 11 which is a stable matrix includes a solid phase comprising a synthethic polymer matrix, a karaya matrix, or a matrix of karaya and a synthetic polymer. The solids of the matrix comprise 30% to 50% by weight of the matrix 11. The combination of the mixture is then subjected to irradiation (usually gamma rays) usually to 2.5 mega rads for sterilization. Heretofore, this magnitude of irradiation to mixtures of polysaccharides, such as karaya with a hydric alcohol, preferably glycerol, would cause the matrix to lose dimensional stability with only slight pressure and/or water absorption. Further, the matrix becomes so tacky that it is not manageable as a surgical bandage. Further, if this irradiated karaya is used as a sterile pad to seal drainage as noted in the Hollister U.S. Pat. No. 3,302,647, it may readily break down to a gelatinous substance which may run and break the seal.

The liquid phase of the matrix, such as hydric alcohol, comprises 50% to 70% by weight of the matrix.

The bandage also includes a suitable backing member which may include cotton fabric, woven or standard paper, synthetic fabrics, and plastics. Suitable synthetic fabrics may include nylon or polyester while a suitable plastic backing may include mylar or saran. When the bandage 10 is used as a surgical dressing, the backing element comprises a pervious material such as cotton fabric to permit diffusion of the absorbed liquid into the air.

The substrate 12 also contains a medicinal substance for release to the surface to which the bandage is applied. The medicinal substance is molecularly dispensed in the matrix rather than being encapsulated as in the prior art. The medicinal substance may include an antibacterial, antiseptic, or anti-fungal agents such as boric acid, bacitracin, acriflavine, formaldehyde, gential violet, mercuric sulfide, mercurochrome, neomycin, and PVPiodine. Nitroglycerin may be used as an antianginal agent and hydrocortisone may be used as an anti-inflammatory agent. Suitable anti-pruretic agents include benzoin, calamine, camphor, menthol, phenol, and sulfur. The substrate may also include fragrances such as cinnamon oil, fir needle oil, lemon oil, peppermint oil and spearmint. Suitable healing agents include allantoin, Peruvian balsam, Vitamin A, and Vitamin E. Hormonal agents may include estrogen, progesterone, and testosterone. Protective agents may include benzoin, charcoal, talc, and zinc oxide. Salicylic acid is a suitable keratolytic agent and methyl salicylate is a suitable rubefacient. An exemplary antihistamine is chlorpheniramine.

The bandage also includes a suitable backing member which may include cotton fabric, woven or standard paper, synthetic fabrics, and plastics. Suitable synthetic fabric may include nylon or polyester while a suitable plastic backing may include mylar or saran.

When karaya or other material gums are used in forming the matrix, it is necessary to use polyacrylic acid and/or polyacrylamide to protect karaya during irradiation. However, a predetermined concentration of salts, such as aluminum sulfate or sodium chloride, may be used in the matrix with karaya in some instances in lieu of polyacrylamide and/or polyacrylic acid. For example, concentrations of approximately 6% sodium chloride or aluminum sulfate may be used with karaya in forming the solid phase of the matrix.

It has also been found that vinyl acetate dioctyl maleate copolymer may also be advantageously used in forming the solid phase of the matrix. Vinyl acetate dioctyl maleate copolymer (sold under the trademark "Flexbond 150" by Air Products and Chemicals, Inc., and sold under the trademark "Bostik 8761" by the Bostik Co., Inc.) will intensify the tackiness of the bandage.

|  | Nominal Amounts of Ingredients | Range of Ingredients |
|---|---|---|
| Example 1 | | |
| Polyacrylamide | 5% | 2-20% |
| Karaya | 38% | 10-40% |
| Glycerol | 55% | 50-70% |
| Povidone-Iodine, USP | 2% | 0.1-10% |
| Example 2 | | |
| Polyacrylic acid | 10% | 2-25% |
| Polyacrylamide | 10% | 2-25% |
| Karaya | 18% | 5-30% |
| Glycerol | 60% | 50-70% |
| Povidone-Iodine, USP | 2% | 0.1-10% |
| Example 3 | | |
| Polyacrylamide | 15% | 2-25% |
| Polyacrylic acid | 15% | 2-25% |
| Glycerol | 68% | 50-70% |
| Povidone-Iodine, USP | 2% | 0.1-10% |
| Example 4 | | |
| Polyacrylamide | 30% | 30-50% |
| Glycerol | 62% | 50-70% |
| Methyl salicylate | 8% | 0.1-15% |
| Example 5 | | |
| Polyacrylamide | 21.5% | 2-25% |
| Polyacrylic acid | 12.5% | 2-25% |
| Glycerol | 42% | 50-70% |
| Vinyl acetate-dioctyl maleate | 16% | 10-20% |
| Methyl salicylate | 8% | 0.1-15% |
| Example 6 | | |
| Polyacrylamide | 32% | 20-40% |
| Glycerol | 55% | 50-70% |
| Water | 6% | 1-10% |
| Methyl salicylate | 8% | 0.1-15% |
| Example 7 | | |
| Povidone-Iodine, USP | 2% | 0.1-10% |
| Hydroxy-propylcellulose (Klucel) | 6% | 0.1-10% |
| Glycerin | 56% | 40-70% |
| Water | 6% | 0.1-10% |
| Polyacrylamide (Reten 421) | 30% | 0.1-40% |
| Example 8 | | |
| Povidone-Iodine, USP | 10% | 0.1-15% |
| Reten 421 (polyacrylamide) | 5% | 1-30% |
| Karaya | 35% | 10-45% |
| Glycerol | 50% | 45-75% |
| Example 9 | | |
| Povidone-Iodine, USP | 2% | 0.1-10% |
| Karaya | 43% | 30-50% |
| Glycerol | 55% | 45-50% |
| Example 10 | | |
| Camphor | 2% | 0.1-5% |
| Methylenebisacrylamide | 3% | 0.1-10% |
| Acrylic acid | 8% | 0.1-10% |
| Glycerol | 86% | 45-90% |
| Activators* | 1% | 0.1-2% |
| Example 11 | | |
| Camphor | 2% | 0.1-5% |
| Glycerol | 5% | 45-75% |
| Karaya | 43% | 30-50% |
| Example 12 | | |
| Methyl salicylate | 2% | 0.1-10% |
| Methylene bisacrylamide | 5% | 0.1-10% |
| Acrylic acid | 8% | 0.1-10% |
| Glycerol | 84% | 50-90% |
| Activators (as above) | 1% | 0.1-2% |
| Example 13 | | |
| Methyl salicylate | 8% | 0.1-15% |
| Acrylic acid | 2% | 0.1-10% |
| Methylenebisacrylamide | 1% | 0.1-10% |
| Glycerol | 48% | 45-75% |
| Karaya | 40% | 10-50% |
| Activators | 1% | 0.1-2% |
| Example 14 | | |
| Methyl salicylate | 8% | 0.1-15% |
| Karaya | 45% | 10-50% |

| | Nominal Amounts of Ingredients | Range of Ingredients |
|---|---|---|
| Glycerol | 47% | 40-75% |

*Potassium persulfate 0.6%
Sodium metabisulfite 0.2%
Ferrous sulfate 0.1%

What is claimed is:

1. A flexible, liquid-abosrbent, adhesive bandage to be applied to a patient comprising:
   a flexible backing element selected from the group comprised of cotton, paper, synthetic fabric and plastic,
   a substrate attached to said backing element comprising a homogeneous, hydrophilic, stable matrix having adhesive properties for adhesion to the skin and being sufficiently pliant to conform to the shape of the body contours, said matrix including a solid phase comprising about 30% to 50% of the total weight of the matrix and including a synthetic resin selected from the group comprising polyacrylic acid, polyacrylamide and their cogeners, and a liquid phase consisting of a solution or emulsion of carbohydrate and/or protein and comprising from about 50% to 70% by weight of the matrix, said matrix having been sterilized by irradiation and containing a medicament selected from the group including anti-anginal agent, antibacterial agent, antiseptic agent, antifungal agent, anti-histamine agent, anti-inflammatory agent, anti-pruretic agent, hormonal agent, keratolytic agent, skin protective agent, and a rubefacient agent.

2. The bandage as defined in claim 1 wherein said liquid phase comprises a solution of a polysacharride.

3. The bandage as defined in claim 1 wherein said liquid phase comprises a hydric alcohol such as glycerol.

4. The bandage as defined in claim 1 wherein the solid phase of matrix includes a natural gum selected from the group comprising karaya, gum acacia, locust bean gum and guar gum.

5. The bandage as defined in claim 4 wherein said liquid phase comprises glycerol.

6. The bandage as defined in claim 4 wherein said matrix is comprised of 10% to 40% by weight of karaya, 2% to 20% by weight of polyacrylamide, and 50% to 70% by weight of glycerol.

7. The bandage as defined in claim 1 wherein said matrix is comprised of 30% to 50% by weight of polyacrylamide and 50% to 70% by weight of glycerol.

8. The bandage as defined in claim 1 wherein said matrix is formed 2% to 25% by weight of polyacrylamide and 2% to 25% by weight of polyacrylic acid, and 50% to 70% by weight of glycerol.

9. The bandage as defined in claim 1 wherein said matrix is formed of 30% to 50% by weight of polyacrylic acid and 50% to 70% by weight of glycerol.

10. The bandage as defined in claim 3 wherein said medicament comprises 0.1% to 15% by weight of PVP-Iodine.

11. The bandage as defined in claim 3 wherein said medicament comprises 0.1% to 5% by weight of camphor.

12. The bandage as defined in claim 4 wherein said medicament comprises 0.1% to 5% by weight of camphor.

13. The bandage as defined in claim 3 wherein said medicament comprises 0.1% to 15% by weight of methyl salicylate.

* * * * *